United States Patent
Korkala et al.

(10) Patent No.: US 9,504,396 B2
(45) Date of Patent: Nov. 29, 2016

(54) EXERCISE APPAREL

(75) Inventors: Seppo Korkala, Kempele (FI); Kaisa Lämsä, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 666 days.

(21) Appl. No.: 13/541,925

(22) Filed: Jul. 5, 2012

(65) Prior Publication Data

US 2013/0019383 A1    Jan. 24, 2013

(30) Foreign Application Priority Data

Jul. 19, 2011   (FI) ..................................... 20115759

(51) Int. Cl.
*A61B 5/0408* (2006.01)
*A61B 5/0492* (2006.01)
*A61B 5/00* (2006.01)

(52) U.S. Cl.
CPC ........... *A61B 5/0408* (2013.01); *A61B 5/6804* (2013.01); *A61B 5/0492* (2013.01); *A61B 5/6831* (2013.01)

(58) Field of Classification Search
CPC ... A61B 5/6804; A61B 5/6805; A61B 5/6831; A61B 5/0408; A61B 5/0478; A61B 5/0492; A61B 5/0533
USPC ....... 600/372, 382, 386, 388, 389, 390, 395, 600/301, 509
See application file for complete search history.

(56) References Cited

U.S. PATENT DOCUMENTS

| | | | | |
|---|---|---|---|---|
| 3,322,554 A | * | 5/1967 | Wyss et al. | 428/90 |
| 3,534,727 A | * | 10/1970 | Roman | 600/389 |
| 3,542,010 A | * | 11/1970 | Love | 600/384 |
| 4,356,818 A | * | 11/1982 | Macias et al. | 128/886 |
| 5,143,089 A | * | 9/1992 | Alt | A61N 1/3918 600/374 |
| 5,725,707 A | * | 3/1998 | Koon et al. | 156/157 |
| 2006/0004273 A1 | * | 1/2006 | Lobodzinski | A61B 5/0408 600/395 |
| 2006/0142654 A1 | | 6/2006 | Rytky | |
| 2007/0032717 A1 | * | 2/2007 | Brister | A61B 5/14532 600/347 |
| 2007/0060815 A1 | * | 3/2007 | Martin | A61B 5/0408 600/372 |
| 2007/0078324 A1 | | 4/2007 | Wijisiriwardana | |
| 2007/0238944 A1 | * | 10/2007 | Axelgaard | A61N 1/0452 600/372 |
| 2007/0285868 A1 | * | 12/2007 | Lindberg | A61B 5/0245 600/382 |
| 2008/0287770 A1 | * | 11/2008 | Kurzweil et al. | 600/388 |
| 2011/0087115 A1 | * | 4/2011 | Sackner et al. | 600/484 |
| 2013/0144131 A1 | * | 6/2013 | Wang et al. | 600/301 |
| 2013/0197341 A1 | * | 8/2013 | Grob | A61N 1/0472 600/391 |
| 2013/0211208 A1 | * | 8/2013 | Varadan et al. | 600/301 |
| 2014/0052111 A1 | * | 2/2014 | Odermatt et al. | 604/543 |
| 2014/0135608 A1 | * | 5/2014 | Gazzoni et al. | 600/395 |
| 2014/0343391 A1 | * | 11/2014 | Korkala et al. | 600/393 |

FOREIGN PATENT DOCUMENTS

DE    202007017033 U1    2/2008

OTHER PUBLICATIONS

Vilja Voutilainen, Finnish Official Action for corresponding Finnish Application No. 20115759, p. 1, May 16, 2012.

\* cited by examiner

*Primary Examiner* — Linda Dvorak
*Assistant Examiner* — Erin M Cardinal
(74) *Attorney, Agent, or Firm* — Hoffmann & Baron, LLP

(57) ABSTRACT

An apparel is disclosed. The apparel comprises a base layer, at least one electrode layer arranged on the base layer either directly or through at least one intermediate layer. The at least one electrode layer is made at least partly of a conductive material. The apparel further comprises a flocked fiber layer comprising conductive fiber particles arranged on the at least one electrode layer through flocking.

13 Claims, 3 Drawing Sheets

EXERCISE APPAREL

CROSS-REFERENCE TO RELATED APPLICATION

This application claims priority based on Finnish Application No. 20115759, filed Jul. 19, 2011, which is incorporated herein by reference in its entirety.

BACKGROUND

1. Field

The invention relates to the field of sports activities and, particularly, to apparels for use in such activities.

2. Description of the Related Art

Exercise characteristics, such as exercise intensity, can be measured by detecting muscle-generated bioelectric signals on the human skin during an exercise. Examples of bioelectric signals are electrocardiogram ECG (heart) and electromyogram EMG (muscles in general). Bioelectric signals may be non-invasively detected with skin electrodes which are placed on the skin and attached to detection electronics. The skin electrodes may be mounted on apparel, e.g. a strap attached around the body of a user or a shirt worn by the user.

SUMMARY

According to an aspect of the present invention, there is provided an apparel comprising: a base layer; at least one electrode layer arranged on the base layer either directly or through at least one intermediate layer, the at least one electrode layer being made at least partly of a conductive material; and a flocked fibre layer comprising conductive fibre particles arranged on the at least one electrode layer through flocking.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
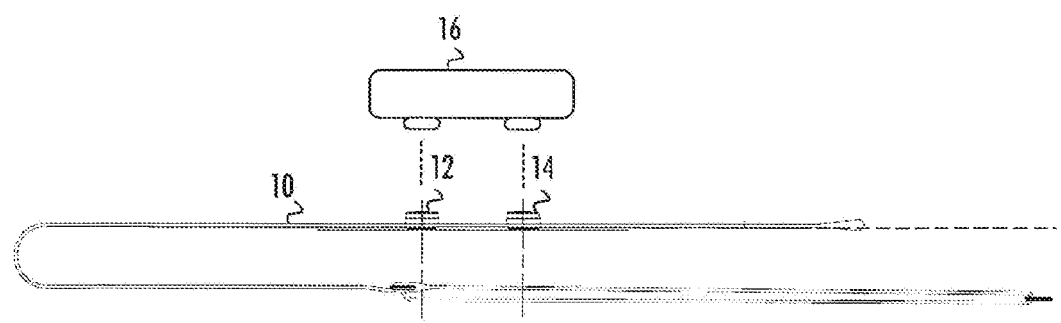
FIGS. 1 to 3 illustrate an apparel to which embodiments of the invention may be applied.

With reference to an embodiment shown in FIG. 1, let us consider an embodiment of an apparel to which embodiments of the invention may be applied. A user-specific sports or activity performance monitor system may comprise a measuring device which may be mounted to said apparel, e.g. a strap 10. The strap 10 may be placed around the chest of a user. It should be noted that the apparel may alternatively be a garment, such as a shirt, a top, a bra, a wristband or trousers. In an embodiment, the garment is a glove, sock, a shirt arm, or a trouser leg. The measuring device may comprise one or more skin electrodes used to receive a physiological signal from the user's skin, and an electronic circuit may be used to process and measure the physiological signal. The electronic circuit may be installed to a casing 16 which may be fixed or detachably attached to the strap 10 through instant connectors 12, 14, such as press stud connectors. The measuring device may also comprise a wireless transmitter circuitry in the casing 16. Then, the measuring device may realize a wireless heart rate transmitter. A signal associated with a signal measured by the electrodes of the measuring device may be wirelessly transmitted from the wireless transmitter circuitry to a receiver, which may be implemented as a PC, laptop, wristband worn on the wrist of the user or as another portable receiver, e.g. a mobile phone. The transmitted signal may carry, for instance, electrocardiography (ECG) information. The location of the receiver is not restricted to the wrist but may be chosen freely, provided that the wireless communication between the belt and the receiver is possible and the user is capable of operating the receiver. Instead of what is presented in FIG. 1, the measuring device provided in the strap alone may act as a user-specific monitor system which may be a portable heart rate monitor.

In an embodiment, the measuring device may be configured to measure, for instance, a physiological signal such as an electromyogram (EMG) from the user's body.

Figure 2:
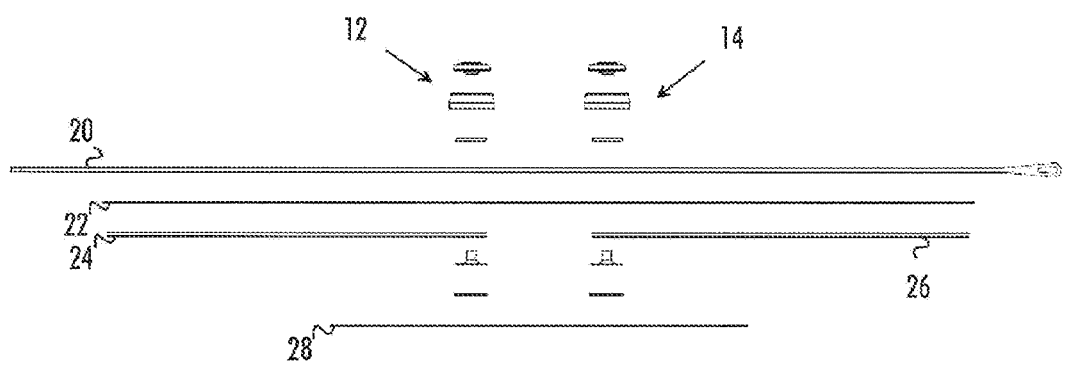
Figure 3:
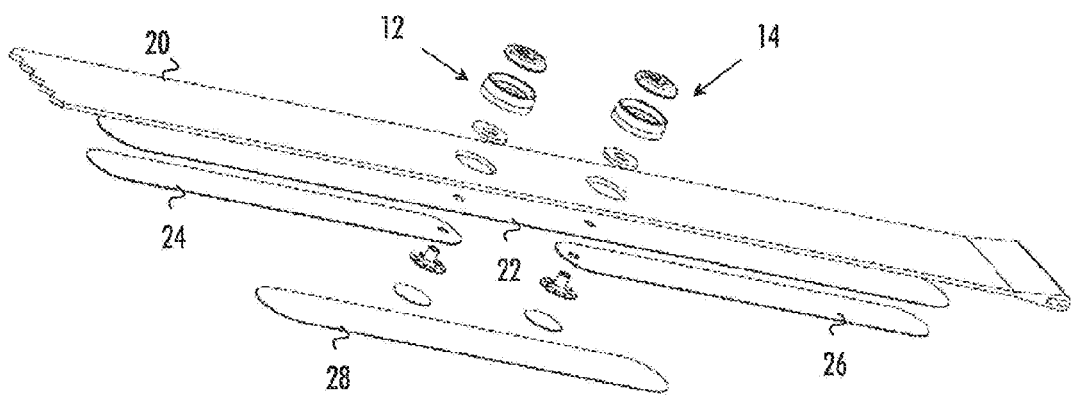

Let us now consider the structure of the apparel in greater detail with reference to an embodiment illustrated in FIGS. 2 and 3. FIGS. 2 and 3 illustrate different explosion views of the components of the apparel, wherein FIG. 2 is a side view, and FIG. 3 is a perspective view. Referring to FIGS. 2 and 3, the apparel comprises a base layer 20. The base layer 20 may form the base of the apparel, and the base layer 20 may comprise textile that forms the apparel, e.g. the strap 10 or the garment. The base layer may comprise woven or knitted textile with elastic components, such as rubber and/or thermoplastic.

The apparel may further comprise an electrode layer comprising one or more electrodes 24, 26 disposed to contact the user's skin either directly or indirectly and to convey electric signals detected from the user's skin to the measuring device connected to the connectors 12, 14. The connectors 12, 14 may be disposed to penetrate the base layer 20 and any layer between the base layer 20 and the electrode layer to provide a galvanic connection between the electrode layer and the measuring device disposed on opposite sides of the base layer 20. In the embodiment shown in FIGS. 2 and 3, the connectors 12, 14 penetrate also the electrode layer, e.g. each electrode 24, 26. A body insulation layer 22 may be provided as an intermediate layer between the base layer 20 and the electrode layer. The body insulation layer 22 functions as an electric insulation layer insulating the electrode layer from the base layer 20. The electrode layer may be made at partially of a conductive material, e.g. conductive silicone.

The number of electrodes 24, 26 may be one, but in some embodiments more than one electrode layer is used. The definition of the electrode layer should be interpreted broadly to cover an electrode layer comprising a plurality of skin electrodes which may be electrically isolated from each other. As a consequence, the electrode layer may comprise a plurality of electrodes 24, 26 separated from each other. One of the skin electrodes may be coupled to a ground, and a physiological signal delivered by at least one other skin electrode may be amplified and measured with respect to the ground. Alternatively, a difference signal detected between the skin electrodes may be amplified and measured with respect to the ground. The ground level may be defined by a skin or a user's body part, such as chest or arm.

When the number of electrodes 24, 26 is higher than one, the electrodes 24, 26 may be electrically isolated from each other. The electrical isolation from a surface contacting the user's skin may be achieved by providing an insulation layer 28 such that the electrodes 24, 26 are at least partially disposed between the isolation layer 28 and the base layer 20. The isolation layer 28 reduces a short circuit between the electrodes 24, 26 through the user's skin. The insulation layer 28 comprises insulating material, such as thermoplastic material, to carry out the isolation. In case the number of electrodes 24, 26 is higher than two, the insulation layer 28 may in some embodiments comprise a plurality of separate insulating portions to insulate the different electrodes 24, 26 from each other.

According to an embodiment of the present invention, the apparel further comprises a flocked fibre layer comprising conductive flocked fibre particles arranged on the at least one electrode layer through a flocking process. Flocking is a process for depositing small fibre particles called flock onto a surface. In the flocking process, fine fibre particles are attached onto a surface coated with adhesive, e.g. glue. The attaching may be carried out applying a high-voltage electric field with which the fibre particles are "shot" onto the adhesive surface. Other flocking techniques comprise spraying using pressured air, reservoir or spray gun. The fibre particles may be given a negative charge while the adhesive surface is earthed. The fibre particles fly onto the adhesive surface attaching to the adhesive. A number of different surfaces can be flocked e.g. textiles, fabric, woven fabric, paper, and plastic.

The flock is also used to refer to a texture produced by the process or to any material forming the flocked surface. In an embodiment, the fibre particles of the flock comprise natural and/or synthetic fibres. In an embodiment, the flock comprises electrically conductive fibre particles, e.g. electrically conductive polymers. The flock may comprise milled flock where the flock is produced from textile waste material. The flock may comprise cut flock where the flock is produced from first quality filament synthetic materials. Generally, the flocked surface is fluffy and velvety which makes it adapt better to the forms of the human body and body motion during an exercise. As a consequence, the flocked surface improves the skin contact of the electrodes. Furthermore, the material of the flocked fibre layer may be moisture-absorbing material which absorbs ionised moisture from the human body or from other sources, thereby further improving the skin contact.

In an embodiment, the conductive fiber particles comprise a substrate component and a doping component. In an embodiment the substrate component comprises electrically insulating material, such as polyester, polyamide or thermoplastic polyurethane (TPU).

In an embodiment, the doping component comprises copper salts.

In an embodiment, the doping component comprises carbon black.

In an embodiment, the doping component comprises metallic powder.

In an embodiment, the doping component comprises intrinsically conducting polymer particles.

In an embodiment, the doping component comprises carbon nanotubes.

In an embodiment, the conductive fibre particles comprise intrinsically conductive polymers.

In an embodiment, an intrinsically conductive polymer comprises polyaniline (PANI).

In an embodiment, an intrinsically conductive polymer comprises polyphenylene vinylene (PPV).

In an embodiment, an intrinsically conductive polymer comprises polyphenylene sulphine (PPS).

In an embodiment an intrinsically conductive polymer comprises polyacetylene (PAC).

In an embodiment, an intrinsically conductive polymer comprises PolyPoly (3,4-ethylenedioxythiophene) (PEDOT).

In an embodiment, an intrinsically conductive polymer comprises polypyrrole (PPY).

In an embodiment, an intrinsically conductive polymer comprises Polythiophene (PTani).

In an embodiment, the intrinsically conductive polymers form the conductive fiber as such.

In an embodiment, the intrinsically conductive polymers are used as doping component with a substrate material.

In an embodiment, the conductive fibre particles comprise metal.

In an embodiment, the metal fibre comprises steel fibres.

In an embodiment, the metal fibre comprises silver fibres.

In an embodiment, the metal fibre comprises gold fibres.

In an embodiment, the metal fibre comprises copper fibres.

Figure 4:
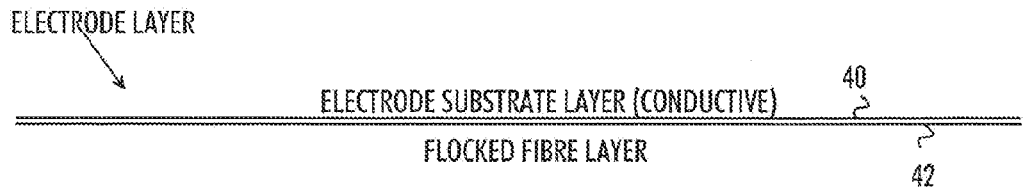
FIGS. 4 and 5 illustrate embodiments of a layered structure of the apparel according to some embodiments of the invention.
Figure 5:
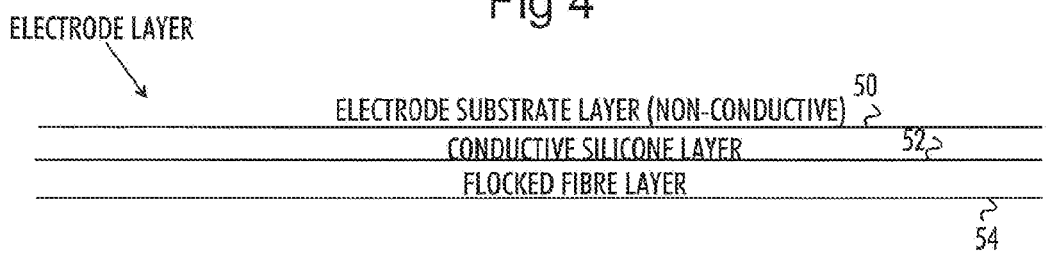

In an embodiment of the invention, a metal fibre is an additive to a substrate material such as polyester or polyamide. FIGS. 4 and 5 illustrate embodiments for a layer structure of the apparel. It should be noted that FIGS. 4 and 5 illustrate only a part of the apparel. In particular, FIGS. 4 and 5 show only a layered structure in a location of an electrode 24, 26 comprised in the apparel. FIGS. 4 and 5 concentrate on the electrode layer and the flocked fibre layer denoted by numeral 42. It should be appreciated that the apparel may comprise other layers as well, e.g. the base layer 20 and one or more intermediate layers. Referring to the embodiment of FIG. 4, the electrode layer may comprise an electrode substrate layer 40 made of conductive material. In an embodiment, the whole electrode substrate layer 40 may be completely made of the conductive material. The conductive material may be conductive plastic or conductive textile, for example. The flocked fibre layer 42 comprising conductive fibre particles may be attached to the electrode substrate layer 40 through the flocking process to realize the flocked surface for the apparel and an electrically conductive path through the flocked fibre layer 42 to the electrode substrate layer 40. The electrode substrate layer 40 may then provide the electric path to the measuring device.

In the embodiment of FIG. 5, the electrode layer comprises a non-conductive electrode substrate layer 50 which functions as a base of the electrode layer. The electrode substrate layer 50 may serve as the body insulation layer 22. In some embodiments, the electrode substrate layer may however, be conductive at least to some degree and, then, a separate body insulation layer 22 may be used. A conductive layer 52 may then be attached to the electrode substrate layer 50 to provide the electrically conductive path to the measuring device. The conductive layer 52 may be made of conductive silicone, for example, as shown in FIG. 5. Then, the flocked fibre layer 54 may be attached to the conductive layer 52 through the flocking process.

In both embodiments of FIGS. 4 and 5, the apparel comprises a plurality of different electrically conductive layers or electrode structures: the conductive flocked fibre layer 42, 54 and another conductive layer, e.g. the electrode substrate layer 40 or the conductive silicone layer 52.

Figure 6:
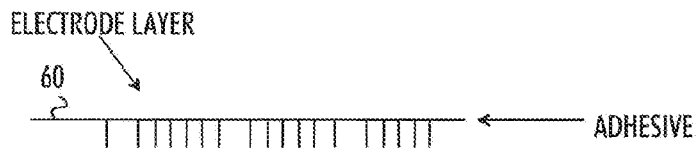
FIG. 6 illustrates another embodiment of the layered structure.

FIG. 6 illustrate another view of the layered structure of the apparel. An adhesive layer 60 may be disposed on the electrode layer, and the conductive flock particles may be shot into the adhesive by applying a potential difference between the conductive flock particles and the electrode layer, thus realizing the fluffy surface shown in FIG. 6 by the vertical lining.

Figure 7:
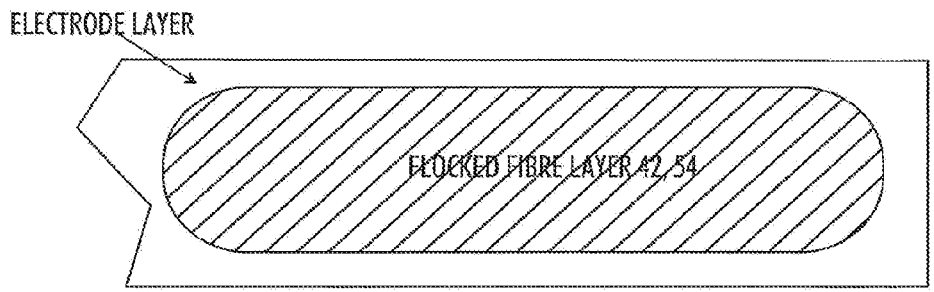
FIGS. 7 to 10 illustrate some embodiments of a flocked fibre layer.

FIGS. 7 to 10 illustrate different embodiments related to the flocked fibre layer 42, 54. In the embodiment of FIG. 7, the flocked fibre layer 42, 54 covers the electrode layer completely. The flocked fibre layer 42, 54 may also extend to cover the apparel in other areas where the electrode layer is not provided.

Figure 8:
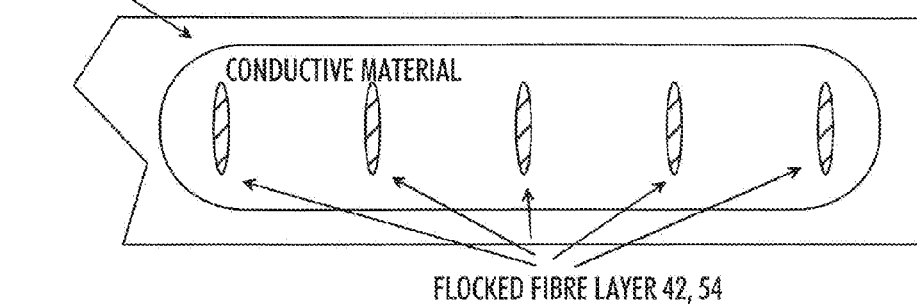
Figure 9:
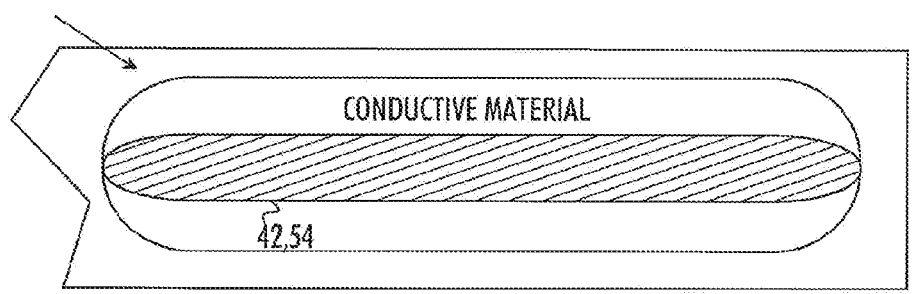
Figure 10:
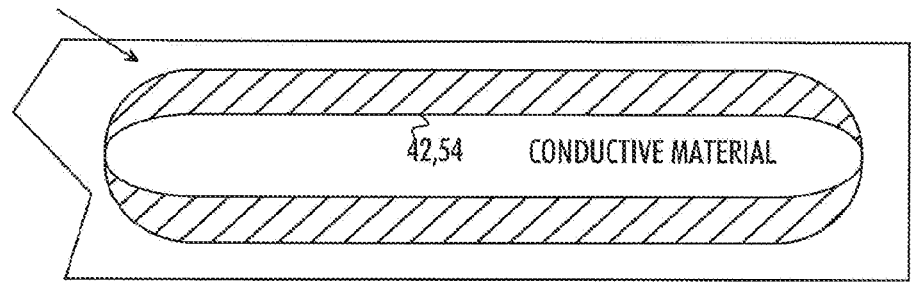

In the embodiments of FIGS. 8 to 10, the flocked fibre layer 42, 54 covers the electrode layer partially, thus leaving other parts of the electrode layer exposed (visible). In some embodiments, the other parts of the electrode layer may be covered by another coating, e.g. the insulation layer 28. In some embodiments, the flocked fibre layer 42, 54 covers at least half of the surface area of the electrode layer.

In the embodiment of FIG. 8, the flocked fibre layer 42, 54 is realized by separated areas of the flocking material disposed on the electrode layer. The number of such areas and their respective sizes may selected as desired, e.g. to form a desired pattern.

In the embodiment of FIG. 9, the flocked fibre layer 42, 54 is provided as a uniform layer on the electrode layer. In this embodiment, the flocked fibre layer 42, 54 is provided in the middle of the electrode layer, thus leaving at least some of the edges of the electrode layer exposed. In the embodiment of FIG. 10, the edges of the electrode layer are covered by the flocked fibre layer, thus leaving the centre of the electrode layer exposed.

The flocked fibre layer 42, 54 functions as a conductive coating provided on the electrode layer and, thus, provides a comfortable skin contact as well as an improved electrical contact between the skin and the electrode layer. It should be appreciated that the flocked fibre layer 42, 54 may be arranged to provide arbitrary shapes on the electrode layer. The thickness of the flocked fibre layer may be adjusted by appropriate selection of the flocking material. Coarse fibre particles provide fluffier surface, while smaller fibre particles provide a smoother surface. The soft flocked surface feels comfortable for the user, and it also adapts well to the motion of the apparel with respect to the user's skin, e.g. during an exercise, thus improving the electric contact, as described above. It will be obvious to a person skilled in the art that, as technology advances, the inventive concept can be implemented in various ways. The invention and its embodiments are not limited to the examples described above but may vary within the scope of the claims.

What is claimed is:

1. An apparel comprising:
    a base layer;
    a plurality of different electrically conductive layers comprising:
        at least one electrode layer arranged on the base layer either directly or through at least one intermediate layer, the at least one electrode layer being made at least partly of a conductive material;
        an adhesive layer arranged on the at least one electrode layer; and
        a flocked fibre layer comprising conductive fibre particles arranged on the adhesive layer through flocking, wherein the conductive fibre particles of the flocked fibre layer comprise a substrate component of electrically insulating material and a doping component, wherein the doping component comprises metal fibres, carbon nanotubes, or at least one of the following types of intrinsically conducting polymer particles: polyphenylene vinylene, polyphenylene sulphine, polyacetylene, poly(3,4-ethylenedioxythiophene), polypyrrole, polythiophene; and
    an isolation layer comprising insulating material, wherein the plurality of different electrically conductive layers is at least partially disposed between the isolation layer and the base layer.

2. The apparel of claim 1, wherein the flocked fibre layer has a fluffy surface of said conductive fibre particles.

3. The apparel of claim 1, wherein the flocked fibre layer covers the at least one electrode layer completely.

4. The apparel of claim 1, wherein the flocked fibre layer covers the at least one electrode layer only partially.

5. The apparel of claim 1, wherein a surface of the electrode layer that contacts with the flocked fibre layer comprises conductive material and is a conductive surface.

6. The apparel of claim 5, wherein the electrode layer further comprises a non-conductive electrode substrate layer, and wherein the conductive surface of the electrode layer is between the electrode substrate layer and the flocked fibre layer.

7. The apparel of claim 5, wherein the conductive surface comprises conductive silicone.

8. The apparel of claim 1, wherein the base layer comprises a textile layer.

9. The apparel of claim 8, wherein the apparel is a garment.

10. The apparel of claim 8, wherein the apparel is a strap.

11. The apparel of claim 1, further wherein the doping component comprises intrinsically conductive polymer particles.

12. The apparel of claim 1, wherein the flocked fibre layer is moisture absorbing.

13. The apparel of claim 1, wherein the flocked fibre layer extends to cover the apparel in an area where the electrode layer is not provided.

* * * * *

UNITED STATES PATENT AND TRADEMARK OFFICE
CERTIFICATE OF CORRECTION

PATENT NO.        : 9,504,396 B2           Page 1 of 1
APPLICATION NO.   : 13/541925
DATED             : November 29, 2016
INVENTOR(S)       : Seppo Korkala and Kaisa Lämsä

It is certified that error appears in the above-identified patent and that said Letters Patent is hereby corrected as shown below:

In the Specification

Column 3, Line 35:
Now reads: "may be carried out applying"
Should read: --may be carried out by applying--

Column 5, Line 34:
Now reads: "may selected as desired"
Should read: --may be selected as desired--

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*